(12) United States Patent
Smith

(10) Patent No.: US 6,982,567 B2
(45) Date of Patent: *Jan. 3, 2006

(54) COMBINATION OPTICAL AND ELECTRICAL METROLOGY APPARATUS

(75) Inventor: Walter Lee Smith, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/843,192

(22) Filed: May 11, 2004

(65) Prior Publication Data

US 2004/0207427 A1  Oct. 21, 2004

Related U.S. Application Data

(60) Continuation of application No. 10/205,868, filed on Jul. 26, 2002, now Pat. No. 6,791,310, which is a division of application No. 09/519,051, filed on Mar. 3, 2000, now abandoned.

(60) Provisional application No. 60/124,715, filed on Mar. 15, 1999.

(51) Int. Cl.
   *G01R 31/26*  (2006.01)
(52) U.S. Cl. .................................. 324/765; 324/158.1
(58) Field of Classification Search ........ 324/750–753, 324/763–765, 96, 501; 438/14–18; 356/400, 356/364
   See application file for complete search history.

(56) References Cited

U.S. PATENT DOCUMENTS

| 4,393,348 | A |   | 7/1983  | Goldstein et al. ........... 324/765 |
| 5,369,495 | A |   | 11/1994 | Lagowski .................. 356/418 |
| 5,493,236 | A |   | 2/1996  | Ishii et al. .................. 324/752 |
| 5,594,247 | A |   | 1/1997  | Verkuil et al. .............. 250/326 |
| 5,773,989 | A |   | 6/1998  | Edelman et al. ............ 324/765 |
| 5,834,941 | A |   | 11/1998 | Verkuil ....................... 324/455 |
| 5,977,788 | A |   | 11/1999 | Lagowski ................... 324/765 |
| 5,999,002 | A |   | 12/1999 | Fasnacht et al. ............ 324/525 |
| 6,791,310 | B2 | * | 9/2004  | Smith ......................... 324/765 |

OTHER PUBLICATIONS

"A Novel Method for Studying Degradation Related to Plasma Processing of Silicon Wafers," J.Lagowski, *Research Society Spring Meeting*, Apr. 1996, San Francisco, CA.

"Contact potential difference methods for full wafer characterization of oxidized silicon," J. Lagowski, *DRIP VII, 7th International Conference on Defects Recognition and Image Processing in Semiconductors*, Sep. 7-10, 1997, Templin, Germany.

"Improving wafer defect and impurity prevention with carrier lifetime measurements," W.H. Howland, Jr., *Solid State Technology*, Sep. 1997.

(Continued)

*Primary Examiner*—Vinh P. Nguyen
(74) *Attorney, Agent, or Firm*—Stallman & Pollock LLP

(57) ABSTRACT

A combination metrology tool is disclosed for analyzing samples, and in particular semiconductor samples. The device includes a first measurement module for determining electrical characteristics of the sample. In general, such a measurement module will monitor electrical characteristics to derive information such as carrier lifetimes, diffusion lengths and surface doping. The device also includes a second measurement module for determining compositional characteristics such as layer thickness, index of refraction and extinction coefficient. The second measurement module will include a light source for generating a probe beam which interacts with the sample. A detection system is provided for monitoring either the change in magnitude or polarization state of the probe beam. The output signals from both measurement modules are combined by a processor to more accurately evaluate the sample.

10 Claims, 1 Drawing Sheet

OTHER PUBLICATIONS

"Real-time, preparation-free imaging of mobile charge of $SiO_2$," L. Jastrzebski, *Optical Characterization Techniques for High-Performance Microelectronic Manufacturing (SPIE Proceedings)*, vol. 2877, Oct. 16-17, 1996, Austin, TX.

"'Cocos'Metrology—Application for Advanced Gate Dielectrics," J. Lagowski, presented at *SPIE Microelectronics Manufacturing*, Oct. 1997, Austin, TX.

"Monitoring plasma damage: A real-time, noncontact approach," A.M. Hoff, *Solid State Technology*, Jul. 1996 edition.

"EPI—τ—Non-Contact Real Time Methodology for Measuring Generation Lifetime and Resistivity in EPI-Layers," J. Lagowski, presented at *SPIE Microclectronics Manufacturing*, Oct. 1997, Austin, TX.

"A Novel Approach to Monitoring of Plasma Processing Equipment and Plasma Damage Without Test Structures," A. Hoff, *Advanced Semiconductor Manufacturing Conference and Workshop*, Sep. 10-12, 1997, Cambridge, MA.

"A New Approach for Measuring Oxide Thickness," T.G. Miller, *Semiconductor International*, Jul. 1995.

"Replacing C-V Monitoring with Non-Contact COS Charge Analysis," K.B. Catmull, presented at the 1997 *MRS Spring Meeting*,San Francisco, CA.

"COS-Based Q-V Testing: In-line Options of Oxide Charge Monitoring," G.S. Horner, *SEMI/IEEE Advanced Semiconductor Manufacturing Conference & Workshop*, Nov. 13-15, 1995.

"Sequential COCOS and SPV Metrology and Its Application to IC Process Monitoring," A.M. Hoff, *The Electrochemical Society 1999 Joint International Meeting—Honolulu, Hawaii*, Oct. 17-22, 1999.

"A New COCOS Method of Monitoring the Reliability of Ultra-thin Oxides," M. Wilson, *The Electrochemical Society 1999 Joint International Meeting—Honolulu, Hawaii*, Oct. 17-22, 1999.

"Contact Potential Difference Methods for Full Wafer Characterization of Si/SiO2 Interface Defects Induced by Plasma Processing," P. Edelman, *SPIE*, vol. 3509, Sep. 1998, p. 126.

* cited by examiner

COMBINATION OPTICAL AND ELECTRICAL METROLOGY APPARATUS

CLAIM OF PRIORITY

This application is a continuation of U.S. patent application Ser. No. 10/205,868, filed Jul. 26, 2002 now U.S. Pat. No. 6,791,310, which is a divisional of U.S. patent application Ser. No. 09/519,051, filed Mar. 3, 2000, now abandoned, which claims priority to U.S. Provisional Application No. 60/124,715, filed Mar. 15, 1999, each of which is hereby incorporated herein by reference.

TECHNICAL FIELD

The present invention relates to the field of semiconductor metrology tools and, in particular, relates to a tool that combines two complementary types of measurements into a single tool to reduce ambiguities in both types of measurements.

BACKGROUND OF THE INVENTION

In the past, there have been developed a number of devices to measure the electrical parameters of a semiconductor. A typical semiconductor sample might have an oxide layer formed on top of a silicon layer. Additional oxide layers or polysilicon layers can be added on top.

In order to measure the electrical thickness of the layers in a non-contact fashion, a charge is placed on the sample. The capacitance is then measured. The tool can determine electrical thickness based on the equation:

$$t_{electrical} = \in A/C \qquad (1)$$

where t equals the thickness, $\in$ is the electrical permittivity, A is the surface area and C is the capacitance. Permittivity $\in$ is related to the index of refraction (n) by the formula $\in = n^2 \in_0$, where $\in_0$ is the permittivity of free space. Also of interest is the "dielectric constant" $\kappa = \in/\in_0$ and the refractive index $n^2 = \kappa$.

One disadvantage of these electrical metrology devices is that the measurements can be skewed by factors that are either unobservable or are difficult to observe. For example, if the silicon substrate is contaminated with ions, this skews the voltage or capacitance measurements and, thus, the resulting calculations of electrical properties such as electrical thickness of the film.

Furthermore, the determination of at least some electrical properties of the film such as electrical thickness is dependent upon accurate knowledge of the dielectric constant or other inherent properties of the oxide layer. In a typical electrical metrology device, many of the parameters which cannot be measured are assumed to have a particular value. If this assumed value is not correct, the resultant determination of the characteristics of the sample will be incorrect.

Accordingly, it is an object of the subject invention to provide a system which provides multiple independent measurements in order to improve the accuracy of the evaluation of the sample.

BRIEF SUMMARY

In accordance with the subject invention, electrical measurements are improved by providing a separate, independent measurement of at least one of these electrical parameters. One possibility would be to use an optical metrology device to measure thin film thickness. One example of such a device is described in U.S. Pat. No. 5,798,837, issued Aug. 25, 1998, and assigned to the same assignee as herein. This tool combines a number of optical inspection modalities, including spectroscopy and ellipsometry. Each of these modalities is designed to measure composition characteristics of thin films, including thickness and index refraction and extinction coefficient.

If the measurement results from an optical metrology device are combined with the measurement results from an electrical metrology device, the analysis of sample parameters could be improved. For example, the optical metrology device can be used to measure the thickness or index of refraction of the thin film layer. This data can then be used to reduce ambiguities in the electrical measurements. To achieve this result, one might determine an optical thickness value using the optical measurement tool and then substitute that optical thickness value for the electrical thickness in equation 1 above to permit a more accurate determination of the dielectric constant of the sample.

Note that the measurement of the index of refraction is made at optical frequencies ($10^{14}$–$10^{15}$ hertz) while the permittivity (dielectric constant) is typically measured in the megahertz to gigahertz regime.

The subject combination can also be used to improve the evaluation of composition characteristics of the thin films. More specifically, the electrical measurement system could be used to determine the permittivity of the film and using that information as a known parameter (which is related to index of refraction) the additional compositional parameters including thickness and extinction coefficient can be determined based on the optical measurements.

In the above two approaches, one of the sets of measurements is used to determine one parameter which is then used as a known in the calculation of additional parameters using the other set of measurements. Another approach would be to combine all of the measurements into sets of equations which have multiple unknowns and a best-fit solution is found using iterative type calculations such as least square fitting routines. Various other approaches for fitting the data are within the scope of the subject invention.

DETAILED DESCRIPTION

Figure 1:
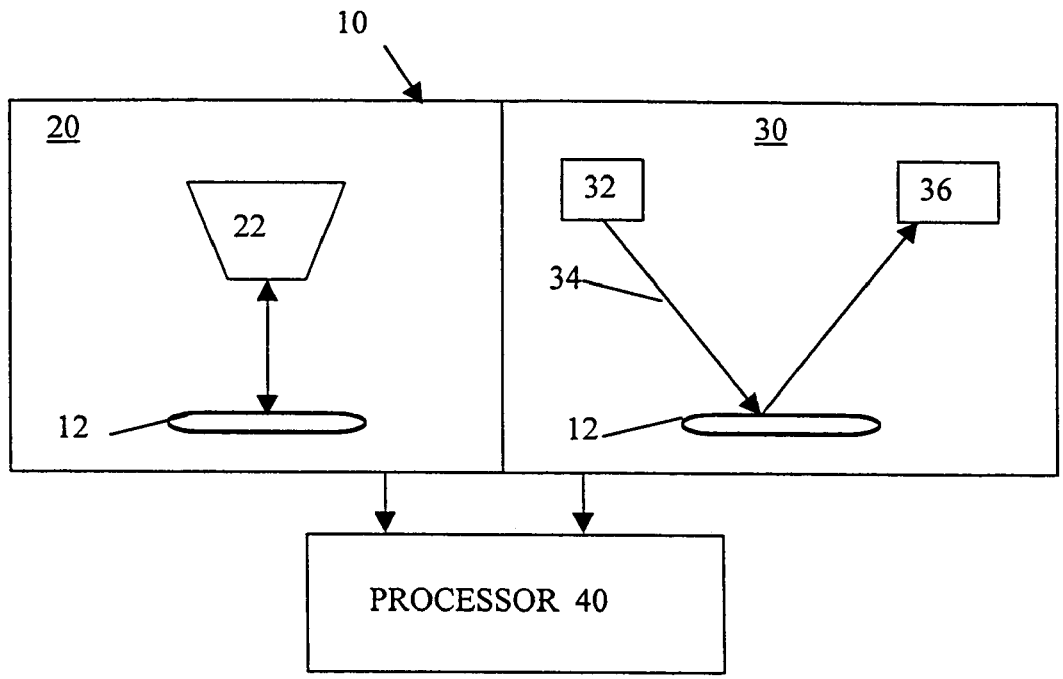
FIG. 1 is a block diagram of the general form of the subject invention.

FIG. 1 illustrates a basic embodiment 10 of the subject invention for use in evaluating characteristics of a sample 12. This device includes a first measurement module 20 which is capable of determining electrical characteristics of the sample. There are many such devices currently on the market. For example, the FAaST series of tools using the COCOS technology (Corona Oxide Characterization of Semiconductor) and EPI-t from Semiconductor Diagnostics and the Quantox Oxide Charge Monitoring System from KLA-Tencor are used to measure electrical characteristics of a sample. Various measurement techniques used in these and other instruments include oxide surface potential, surface photovoltage, contact potential difference, kelvin or mercury probes and corona charge measurements. In FIG. 1, element 22 is intended to generally represent any of these known sensors. These devices are non-contact techniques that rely on some form of voltage or capacitance measurements.

These devices provide information about electrical type characteristics including minority carrier diffusion length, minority carrier lifetime, metal concentration, surface recombination velocity, minority carrier recovery time, surface barrier voltage, oxide voltage, surface space charge, dielectric capacitance, electrical oxide thickness, and surface doping.

For additional background on various devices for determining electrical characteristics of samples, the reader is directed to the publications listed below which are herein incorporated by reference. The scope of the subject invention is intended to include electric measurements made in accordance with any of these or equivalent measurement techniques.

U.S. Pat. No. 5,773,989, by Edelman et al., issued Jun. 30, 1998.

U.S. Pat. No. 5,999,002, by Fasnacht et al., issued Dec. 7, 1999.

U.S. Pat. No. 5,834,941, by Verkuil, issued Nov. 10, 1998.

U.S. Pat. No. 5,594,247, by Verkuil et al., issued Jan. 14, 1997.

U.S. Pat. No. 5,977,788, by Lagowski, issued Nov. 2, 1999.

U.S. Pat. No. 5,369,495, by Lagowski, issued Nov. 29, 1994.

"A Novel Method for Studying Degradation Related to Plasma Processing of Silicon Wafers," J. Lagowski, *Research Society Spring Meeting*, April 1996, San Francisco, Calif.

"Contact potential difference methods for full wafer characterization of oxidized silicon," J. Lagowski, *DRIP VII, 7th International Conference on Defects Recognition and Image Processing in Semiconductors*, Sep. 7–10, 1997, Templin, Germany.

"Improving wafer defect and impurity prevention with carrier lifetime measurements," W. H. Howland, Jr., *Solid State Technology*, September 1997.

"Real-time, preparation-free imaging of mobile charge of $SiO_2$," L. Jastrzebski, *Optical Characterization Techniques for High-Performance Microelectronic Manufacturing (SPIE Proceedings)*, Vol. 2877, Oct. 16–17, 1996, Austin, Tex.

"Cocos' Metrology—Application for Advanced Gate Dielectrics," J. Lagowski, presented at *SPIE Microelectronics Manufacturing*, Octotober 1997, Austin, Tex.

"Monitoring plasma damage: A real-time, noncontact approach," A. M. Hoff, *Solid State Technology*, July 1996 edition.

"EPI-τ-Non-Contact Real Time Methodology for Measuring Generation Lifetime and Resistivity in EPI-Layers," J. Lagowski, presented at *SPIE Microelectronics Manufacturing*, October 1997, Austin, Tex.

"A Novel Approach to Monitoring of Plasma Processing Equipment and Plasma Damage Without Test Structures," A. Hoff, *Advanced Semiconductor Manufacturing Conference and Workshop*, Sep. 10–12, 1997, Cambridge, Mass.

"A New Approach for Measuring Oxide Thickness," T. G. Miller, *Semiconductor International*, July 1995.

"Replacing C-V Monitoring with Non-Contact COS Charge Analysis," K. B. Catmull, presented at the 1997 *MRS Spring Meeting*, San Francisco, Calif.

"COS-Based Q-V Testing: In-line Options for Oxide Charge Monitoring," G. S. Homer, *SEMI/IEEE Advanced Semiconductor Manufacturing Conference & Workshop*, Nov. 13–15, 1995.

"Sequential COCOS and SPV Metrology and Its Application to IC Process Monitoring," A. M. Hoff, *The Electrochemical Society* 1999 *Joint International Meeting—Honolulu Hi.*, Oct. 17–22, 1999.

"New COCOS Method for Monitoring the Reliability of Ultra-thin Oxides," M. Wilson, *The Electrochemical Society* 1999 *Joint International Meeting—Honolulu, Hi.*, Oct. 17–22, 1999.

"Contact Potential Difference Methods for Full Wafer Characterization of Si/SiO2 Interface Defects Induced by Plasma Processing," P. Edelman, SPIE Vol. 3509 September 1998, Page 126.

The subject invention further includes a second measurement module 30 for obtaining non-contact optical measurements of the sample. In such devices, at least one light source 32 is provided for generating a probe beam 34 of radiation. The probe beam is directed to reflect off of the sample 12. A detection system 36 is provided for measuring changes in magnitude and/or polarization state of the probe beam induced by its interaction with the sample. The optical measurement module can include one or more such detection subsystems. As noted above, one suitable measurement module could be patterned after the device disclosed in U.S. Pat. No. 5,798,837, incorporated herein by reference. The device described in this patent includes both laser based and broadband polychromatic measurement technologies. The device is capable of obtaining both reflectometry and ellipsometry measurements. These optical measurements are typically used to determine compositional variables such as thin film thickness, index of refraction and extinction coefficient.

Figure 2:
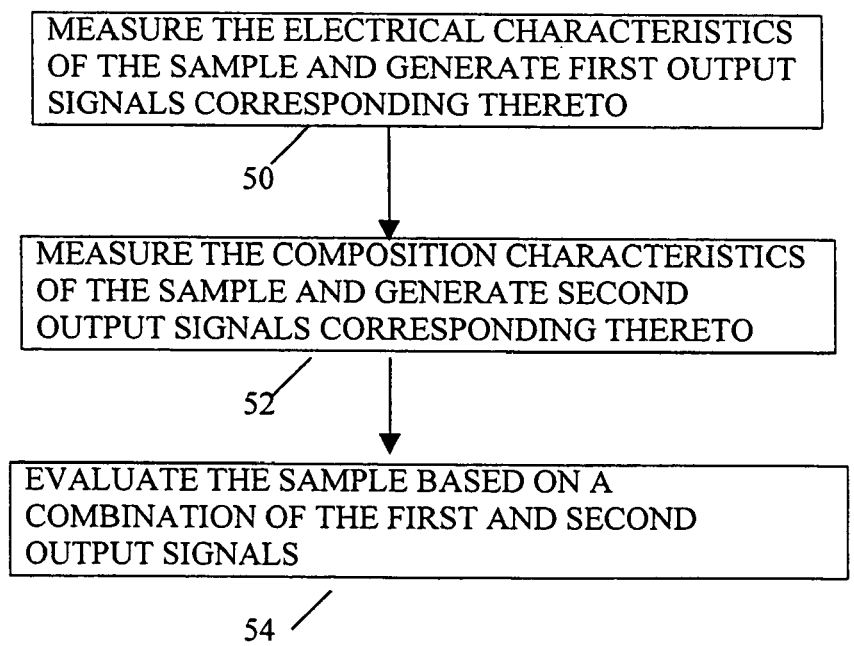
FIG. 2 is a flow chart illustrating the steps to carry out the method of the subject invention.

In accordance with the subject invention, the sample will be measured using each of the tools (steps 50 and 52 in FIG. 2). Preferably, the two measurements will be made close in time to prevent the wafer characteristics from changing. The measurements will be supplied to a processor 40 which can evaluate the sample based on the data generated by both measurement modules (step 54 in FIG. 2). While the processor 40 is shown as part of the system 10, one skilled in the art will understand that the end processor for evaluating the sample can be physically separate from the measurement modules and data can be transferred through a network or via a floppy disc.

There are many possibilities for using both types of data. As discussed above, one set of data could be used to determine one parameter of the sample which then can be used as a known value when computing characteristics of the sample using the remaining set of data. Alternatively, one could combine the data using a fitting algorithm. One skilled in the art could develop appropriate analytical approaches which takes advantage of such multiple measurements.

The combination of the two metrology devices in a single tool, in addition to providing more accurate results, provides economic benefits as well. For example, a single tool has a smaller footprint and therefore takes up less space in the semiconductor fab. By combining technologies in a single tool, costs can be reduced by eliminating duplicate subsystems such as wafer handlers and computers and more rapid process control feedback can be provided. Finally, the combination can simplify and streamline decision making since the information from the two measurement modalities can be coordinated instead of producing conflicting results as in the prior art when two separate devices might be used.

While the subject invention has been described with reference to a preferred embodiment, various changes and modifications could be made therein, by one skilled in the art, without varying from the scope and spirit of the subject invention as defined by the appended claims.

What is claimed is:

1. An apparatus for evaluating a sample comprising:
a first measurement module for performing non-contact electrical measurements of the sample corresponding to electrical characteristics and generating first output signals responsive thereto;
a second measurement module for performing non-contact optical measurements of the sample corresponding to composition characteristics of the sample and generating second output signals responsive thereto; and
a processor for evaluating the sample based on a combination of the electrical and optical measurements represented by said first and second output signals.

2. An apparatus as recited in claim 1, wherein:
the processor evaluates the sample using one of the first or second output signals to characterize one parameter of the sample, and wherein the other of the first and second output signals is used to further characterize the sample wherein said one parameter is treated as a known parameter.

3. An apparatus as recited in claim 1, wherein:
the processor evaluates the sample using the first and second output signals in a fitting algorithm to evaluate both the electrical and the composition characteristics of the sample.

4. An apparatus as recited in claim 1, wherein:
said first measurement module operates using a technique selected from the group consisting of oxide surface potential, surface photovoltage, contact potential difference, Kelvin probe and corona charge measurements.

5. An apparatus as recited in claim 4, wherein:
the measurements made by the first measurement module are used to evaluate at least one parameter selected from the group consisting of minority carrier diffusion length, minority carrier lifetime, metal concentration, surface recombination velocity, minority carrier recovery time, surface barrier voltage, oxide voltage, surface space charge, dielectric capacitance, electrical oxide thickness, surface doping, 6. An apparatus as recited in claim 1, wherein:
the measurements made by the second measurement module are used to evaluate at least one parameter selected from the group consisting of layer thickness, index of refraction and extinction coefficient.

7. An apparatus as recited in claim 1, wherein:
the first measurement module performs non-contact electrical measurements of one of a voltage and a capacitance of the sample.

8. An apparatus as recited in claim 1, further comprising:
a light source capable of directing a probe beam of light to reflect off the sample.

9. An apparatus as recited in claim 8, wherein:
the second measurement module performs non-contact optical measurements of the sample by measuring one of a change in magnitude and polarization state of the probe beam induced by the interaction with the sample in order to generate said second output signals.

10. An apparatus as recited in claim 8, wherein:
the second measurement module further includes a detector for monitoring one of a change in magnitude and polarization state of the probe beam induced by the interaction with the sample.

* * * * *